(12) United States Patent
Hanselmann et al.

(10) Patent No.: US 6,700,010 B1
(45) Date of Patent: Mar. 2, 2004

(54) METHOD FOR PRODUCING CYANOACETIC ACID ESTERS

(75) Inventors: Paul Hanselmann, Brig-Glis (CH); Stefan Hildbrand, Riehen (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/069,579

(22) PCT Filed: Aug. 29, 2000

(86) PCT No.: PCT/EP00/08397

§ 371 (c)(1),
(2), (4) Date: Jul. 12, 2002

(87) PCT Pub. No.: WO01/16092

PCT Pub. Date: Mar. 8, 2001

Related U.S. Application Data

(60) Provisional application No. 60/185,372, filed on Feb. 28, 2000.

(30) Foreign Application Priority Data

Aug. 30, 1999 (EP) .............................. 99117033

(51) Int. Cl.⁷ ............................................ C07C 255/03
(52) U.S. Cl. ...................................................... 558/443
(58) Field of Search ......................................... 558/443

(56) References Cited

U.S. PATENT DOCUMENTS 4,438,041 A   3/1984   Matsui et al.

FOREIGN PATENT DOCUMENTS

WO      WO 92/12962       8/1992

OTHER PUBLICATIONS

B. Wermeckes et al., Electrochim. Acts, vol. 30, No. 11, (1985), pp. 1491–1500.
B. Wermeckes et al., Chem. Ber., (1985), 118(9), 3771–3780.

*Primary Examiner*—Alan L. Rotman
*Assistant Examiner*—Ebenezer Sackey
(74) *Attorney, Agent, or Firm*—Fisher, Christen & Sabol

(57) ABSTRACT

A method for producing cyanoacetic acid esters of general formula (I):

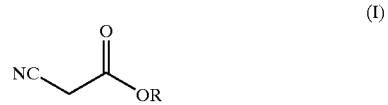

wherein R represents on optionally substituted linear or branched $C_{1-8}$ alkyl group or an aryl $C_{1-4}$ alkyl group. According to the method, an alkoxypropionitrile of the general formula (II):

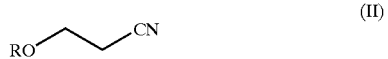

wherein R is defined above, is oxidized to form the desired product in the presence of a catalyst, based on lead or on one of the transition metals, using oxygen or an oxygen-forming reagent.

11 Claims, No Drawings

METHOD FOR PRODUCING CYANOACETIC ACID ESTERS

This is a 371 of International Patent Application PCT/EP00/08397, filed on Aug. 29, 2000, that has priority benefit of Provisional Application No. 60/185,372, filed on Feb. 28, 2000, and that has priority benefit of European Patent Application 99117033.3 filed on Aug. 30, 1999.

The invention relates to a process for the preparation of cyanoacetic acid esters of the, general formula

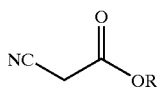

I starting from an alkoxypropionitrile.

The residue R is to be understood here and hereinafter as meaning an optionally substituted linear or branched $C_{1-8}$-alkyl group or an aryl-$C_{1-4}$-alkyl group. Unsubstituted $C_{1-8}$-alkyl groups are, for example, methyl, ethyl, propyl, isopropyl, butyl, isobutyl, tert-butyl, butyl, pentyl, hexyl, 2-ethylbutyl, heptyl, octyl or 2-ethylhexyl. 2-Ethoxyethyl or 2-methoxyethyl may, for example, be employed as substituted $C_{1-8}$-alkyl groups. Aryl-$C_{1-4}$-alkyl groups are, for example, benzyl, 1-phenylethyl and 2-phenylethyl.

Cyanoacetic acid esters of the general formula I are important starting materials for the synthesis of organic compounds, for example pharmaceutical active substances.

The electrochemical oxidation of alkyl β-cyanoethyl ethers (alkoxypropionitrile's) with platinum or lead oxide as anode in aqueous sulfuric acid is known (B. Wermeckes, F. Beck, *Elektrochim. Acta*. 1985, 30, 1491). In this reaction, the main products obtained are not the desired esters but cyanoacetic acid and the carboxylic acid corresponding to the alkyl group such as, for example, formic acid or acetic acid.

WO 92/01296 describes the oxidation of partially oxidized propionitriles (e.g. cyano-acetaldehyde or acetals thereof) by means of oxygen or other oxidants in the presence of catalysts such as iron chloride or palladium chloride, cyanoacetic acid likewise being formed first, which then has to be converted into a cyanoacetic acid ester by acid-catalysed esterification with the appropriate alcohol.

The object of the present invention is to make available a process for the preparation of cyanoacetic acid esters in which the desired cyanoacetic acid esters are formed directly.

This object is achieved by the process according to the invention.

Surprisingly, it has been found that if alkoxypropionitriles of the general formula

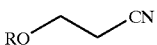

II wherein R has the meaning given above are oxidized using oxygen or an oxygen-forming reagent in the presence of a catalyst based on lead or one of the transition metals, the cyanoacetic acid esters of the general formula I are formed directly.

Depending on the meaning of the radical R and the ester to be produced, starting materials which can be employed are, for example, 3-methoxypropionitrile, 3-ethoxypropionitrile, 3-propoxypropionitrile, 3-butoxypropionitrile and 3-benzyloxypropionitrile. These starting materials are either commercially available compounds or can be prepared according to known syntheses (cf. e.g. B. Wermeckes, F. Beck, *Elektrochim. Acta*, 1985, 30, 1491), for example by addition of the corresponding alcohol to acrylonitrile.

An oxygen-forming reagent which can be used is, for example, hydrogen peroxide.

Transition metals are understood below as meaning, in particular, the metals platinum palladium, ruthenium, rhodium, rhenium, scandium, titanium, vanadium, chromium, manganese, iron, cobalt, nickel, copper, zinc, zirconium, niobium, molybdenum, osmium, silver, cadmium, tantalum, tungsten or mercury.

A cobalt catalyst such as, for example, cobalt acetate tetrahydrate, or cobalt acetylacetonate, is preferably employed for the oxidation.

The cobalt catalyst most preferably employed is cobalt acetate tetrahydrate.

Preferably, the transition metal catalyst is employed in an amount from 0.01 to 10 mol %, more preferably in an amount from 0.01 to 3 mol %.

The oxidation is expediently carried out at a temperature of 50 to 250° C., preferably at a temperature of 100 to 200° C.

The oxidation is customarily carried out under pressure, such as, for example, a pressure of 5 to 15 bar.

The oxidation is carried out either without solvent or in an inorganic or organic solvent. The organic solvent employed can be, for example, acetonitrile, acetic acid, toluene, ethyl acetate, acetone or tetrahydrofuran, or an alcohol such as methanol, ethanol, propanol or butanol. The inorganic solvent used can be, for example, water. An organic solvent such as acetonitrile is preferably employed.

The oxidation is expediently carried out in the presence of a radical inducer such as, for example, N-hydroxyphthalimide, N-hydroxysuccinimide or N-hydroxymaleimide.

The following non-limiting examples will illustrate the implementation of the process of the invention.

EXAMPLE 1

Methyl Cyanoacetate 1.1 9 bar of $O_2$ were injected into a solution of 3.0 g (0.035 mol) of 3-methoxypropionitrile (Fluka), 0.5 g (3.0 mmol) of NHPI (N-hydroxy-phthalimide) and 57 mg (0.23mmol) of $Co(CH_3COO)_2 \cdot 4H_2O$ in 50 ml of acetic acid in a pressure autoclave. The mixture was subsequently stirred at 150° C. for 5 h. The pressure in the autoclave was released and the reaction mixture was analysed by gas chromatography. The starting material/product ratios were determined by comparison of the respective peak areas. The apparatus used was an HP 5890 gas chromatograph having a WLD detector and Permabond® Carbowax column. A ratio 3-methoxypropionlitrile/methyl cyano-acetate of 11:1 was found.

1.2 9 bar of $O_2$ were injected into a solution of 3.0 g (0.035 mol) of 3-methoxypropionitrile, 1.0 g (6.13 mmol) of NHPI and 112 mg (0.45 mmol) of $Co(CH_3COO)_2 \cdot 4H_2O$ in 30 g of acetonitrile. The mixture was stirred at 190° C. for 7 h. The pressure in the autoclave was released and the reaction mixture was analysed by gas chromatography according to Example 1.1. A ratio 3-methoxypropio-nitrile/methyl cyanoacetate of 2:1 was found. The reaction was then worked up: acetonitrile was distilled off on a rotary evaporator, the residue was taken up in 50 ml of diethyl ether and the mixture was filtered. The filtrate was washed with H₂O (50 ml), the solvent was stripped off on the rotary evaporator and the residue was purified by means of flash column chromatography (hexane/ethyl acetate 3:1). The complete separation of the starting material was not possible.

¹H-NMR (CDCl₃, 300 MHz) δ: 3.81 (s, 3H), 3.5 (s, 2H).

1.3 9 bar of O₂ were injected into a solution of 1.0 g (6.13 mmol) of NHPI and 100 mg (0.40 mmol) of Co(CH₃COO)₂.4H₂O in 20.0 g (0.23 mol) of 3-methoxypropionitrile. The mixture was stirred at 130° C. for 3 h and the pressure in the autoclave was then released. According to GC corresponding to Example 1.1, a ratio of 9:1 (starting material/methyl cyanoacetate) was obtained.

1.4 9 bar of O₂ were injected into a solution of 6.0 g (0.07 mol) of 3-methoxypropionitrile, 2.5 g (0.015 mol) of NHPI and 0.5 g (2 mmol) of Co(CH₃COO)₂.4H₂O in 30 g of acetonitrile. The mixture was stirred at 180° C. for 5.5 h. The pressure in the autoclave was released and the reaction mixture was analysed by gas chromatography corresponding to Example 1.1. A ratio starting material/methyl cyanoacetate of 5:1 was found.

EXAMPLE 2

Ethyl Cyanoacetate 9 bar of O₂ were injected into a solution of 3.0 g (0.030 mol) of 3-ethoxypropionitrile, 1.0 g (6.13 mmol) of NHPI and 116 mg (0.47 mmol) of Co(CH₃COO)₂.4H₂O in 30 g of acetonitrile. The mixture was stirred at 190° C. for 7 h. The pressure in the autoclave was released and the reaction mixture was analysed by gas chromatography corresponding to Example 1.1. A ratio starting material/ethyl cyanoacetate of 3:1 was found.

The results of the examples are summarized in Table 1.

TABLE 1

| Example | R = | Cat [mol %] | NHPI [mol %] | Solv. | ϑ [° C.]/ t [h] | Starting material/ product |
|---|---|---|---|---|---|---|
| 1 | Me | 0.65 | 8.6 | Acetic acid | 150/5 | 11:1 |
| 2 | Me | 1.3 | 17.5 | Acetonitrile | 190/7 | 2:1 |
| 3 | Me | 0.17 | 2.6 | None | 130/3 | 9:1 |
| 4 | Me | 2.9 | 21.8 | Acetonitrile | 180/5.5 | 5:1 |
| 5 | Et | 1.5 | 20.3 | Acetonitrile | 190/7 | 3:1 |

Abbreviations: Me = methyl, Et = ethyl, Cat = catalyst, NHPI = N-hydroxyphthalimide, Solv. = solvent

What is claimed is:

1. A process for the preparation of a cyanoacetic acid ester of formula:

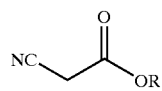

in which R is an optionally substituted linear or branched C₁₋₈-alkyl group or an aryl- C₁₋₄-alkyl group, comprising oxidizing an alkoxypropionitrile of formula:

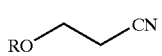

in which R has the meaning given above, using oxygen or an oxygen-forming reagent to give the cyanoacetic acid ester of formula I, in the presence of a catalyst based on lead or one of the transition metals.

2. The process according to claim 1, wherein the transition metal catalyst is a cobalt catalyst.

3. The process according to claim 2, wherein the cobalt catalyst is cobalt(II) acetate tetrahydrate.

4. The process according to claim 3, wherein the cobalt(II) acetate tetrahydrate is employed in an amount from 0.01 to 10 mol percent relative to the alkoxypropionitrile of formula II.

5. The process according to claim 4, wherein the oxidation is carried out at a temperature of 50 to 250° C.

6. The process according to claim 5, wherein the oxidation is carried out in an organic solvent.

7. The process according to claim 1, wherein the cobalt catalyst is cobalt(II) acetate tetrahydrate.

8. The process according to claim 1, wherein the transition metal catalyst is employed in an amount from 0.01 to 10 mol percent relative to the alkoxypropionitrile of formula II.

9. The process according to claim 1, wherein the oxidation is carried out at a temperature of 50 to 250° C.

10. The process according to claim 1, wherein the oxidation is carded out in an organic solvent.

11. The process according to claim 1, wherein the oxidation includes a radical inducer selected from the group consisting of N-hydroxyphthalimide, N-hydroxysuccinimide and N-hydroxymaleimide.

* * * * *